United States Patent
Suwa et al.

(10) Patent No.: US 8,445,718 B2
(45) Date of Patent: May 21, 2013

(54) METHOD FOR PRODUCING PHOSPHONIC ACID METAL SALT FINE PARTICLES

(75) Inventors: Takeshi Suwa, Funabashi (JP); Hisato Hayashi, Funabashi (JP); Masaaki Ozawa, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/266,962

(22) PCT Filed: May 12, 2010

(86) PCT No.: PCT/JP2010/058048
§ 371 (c)(1),
(2), (4) Date: Oct. 28, 2011

(87) PCT Pub. No.: WO2010/131678
PCT Pub. Date: Nov. 18, 2010

(65) Prior Publication Data
US 2012/0046397 A1 Feb. 23, 2012

(30) Foreign Application Priority Data

May 12, 2009 (JP) .................................. 2009-116020

(51) Int. Cl.
*C07F 9/28* (2006.01)

(52) U.S. Cl.
USPC ................. 562/24; 562/23; 524/132; 524/135

(58) Field of Classification Search
USPC ................................. 524/132, 135; 562/23, 24
See application file for complete search history.

(56) References Cited

U.S. PATENT DOCUMENTS

2007/0299170 A1  12/2007  Ozawa et al.

FOREIGN PATENT DOCUMENTS

| JP | A-08-003432 | 1/1996 |
| JP | A-10-087975 | 4/1998 |
| JP | A-10-158369 | 6/1998 |
| JP | A-2003-192883 | 7/2003 |
| JP | A-2008-156616 | 7/2008 |
| JP | A-2008-247956 | 10/2008 |
| WO | WO 2005/097894 A1 | 10/2005 |

OTHER PUBLICATIONS

Hayashi et al., "Reaction of the Phenylphosphonate Anion with the Layered Basic Copper(II) Nitrate [$Cu_2(OH)_3NO_3$]," *J. Mater. Chem.*, 1995, vol. 5, No. 1, pp. 115-119.

Bellitto et al., "Synthesis, X-ray Powder Structure, and Magnetic Properties of the New, Weak Ferromagnet Iron(II) Phenylphosphonate," *Inorg. Chem.*, 2000, vol. 39, pp. 1803-1808.
Svoboda et al., "Synthesis and characterization of new potential intercalation hosts-barium arylphosphonates," *Journal of Physics and Chemistry of Solids*, 2008, vol. 69, pp. 1439-1443.
Zima et al., "New strontium phenylphosphonate: synthesis and characterization," *Solid State Sciences*, 2006, vol. 8, pp. 1380-1385.
Scott et al., "Synthesis, Characterization, and Amine Intercalation Behavior of Zinc Phosphite Phenylphosphonate Mixed Derivatives," *Chem. Mater.*, 1995, vol. 7, pp. 1095-1102.
Song et al., "Selected-Control Synthesis of Metal Phosphonate Nanoparticles and Nanorods," *Inorg. Chem.*, 2005, vol. 44, No. 7, pp. 2140-2142.
International Search Report in International Application No. PCT/JP2010/058048; dated Jun. 22, 2010 (with English-language translation).
Written Opinion of the International Searching Authority in International Application No. PCT/JP2010/058048; dated Jun. 22, 2010 (with English-language translation).
Mar. 7, 2013 Extended European Search Report issued in European Patent Application No. 10 77 4935.
Bauer et al., "Comparison of the Structure and Magnetic Order in a Series of Layered Ni(II) Organophosphonates, $Ni[(RPO_3)(H_2O)]$ ($R=C_6H_5$, $CH_3$, $C_{18}H_{37}$)," Inorganic Chemistry, vol. 47, No. 23, Nov. 1, 2008, pp. 10945-10952.
Song et al., "Selected-Control Synthesis of Metal Phosphonate Nanoparticles and Nanorods," Inorganic Chemistry, vol. 44, No. 7, Mar. 10, 2005, pp. 2140-2142.

*Primary Examiner* — Peter Szekely
(74) *Attorney, Agent, or Firm* — Oliff & Berridge, PLC

(57) ABSTRACT

There is provided to a method for efficiently producing phosphonic acid metal salt fine particles with an average particle diameter of 0.5 μm or less with high efficiency. A method for producing phosphonic acid metal salt fine particles, comprising: a) causing a reaction of a phosphonic acid compound of Formula (I):

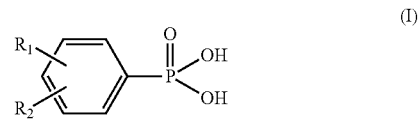

(I)

(where $R_1$ and $R_2$ are each independently a hydrogen atom, an alkyl group having 1 to 10 carbon atoms, or an alkoxycarbonyl group having 1 to 10 carbon atoms) with a base in an aqueous medium to adjust a pH range of the reaction system to be neutral to basic; b) causing a reaction of the product obtained in a) with a metal salt to precipitate a phosphonic acid metal salt from the aqueous medium; c) removing water from the phosphonic acid metal salt precipitated in b); and d) heating and drying the phosphonic acid metal salt from which water is removed in c).

7 Claims, 9 Drawing Sheets

METHOD FOR PRODUCING PHOSPHONIC ACID METAL SALT FINE PARTICLES

TECHNICAL FIELD

The present invention relates to a method for producing phosphonic acid metal salt fine particles and specifically to a method for producing phosphonic acid metal salt fine particles with an average particle diameter of 0.01 to 0.5 μm with high efficiency.

BACKGROUND ART

Polylactic acid resins that are biodegradable polyester resins are expected to be used as molding materials in various fields, for example, packaging materials such as containers and films, fibrous materials such as clothing, floor mats, and automobile interior materials, housings and parts of electrical and electronic products, and the like.

In order to improve the molding processability and the heat resistance of a polylactic acid resin, attempts have been made to enhance the crystallization rate and the degree of crystallinity of the resin and, as a method for achieving it, addition of a nucleating agent has been developed. The nucleating agent serves as a primary crystal nucleus of a crystalline polymer to facilitate crystal growth, to reduce the crystal size, and to increase the crystallization rate. As nucleating agents for polylactic acid resins, an inorganic particle that includes talc or boron nitride of not larger than a certain particle diameter (Patent Document 1), an amide compound of a certain formula (Patent Document 2), a sorbitol derivative of a certain formula (Patent Document 3), a phosphoric acid ester metal salt of a certain formula (Patent Document 4), phosphonic acid metal salts (Patent Document 5 and Patent Document 6), and the like have been disclosed.

Phosphonic acid metal salts are considered to have excellent performance among these nucleating agents, and are usually produced by causing a reaction of a phosphonic acid-based compound with a metal ion source, for example, a metal hydroxide, a metal oxide, a metal nitrate, or a metal acetate, in water or an organic solvent.

For enhancing the crystallization rate and the degree of crystallinity of the polylactic acid resin, for example, the size of the nucleating agent is reduced. Generally, the smaller the size of the nucleating agent is, the greater the number of particles and the surface area per mass are. In addition, the finer the nucleating agent is, the smaller the size of a polylactic acid resin crystal is. When the particle size of the nucleating agent is small, the transparency of a resin product is enhanced, namely the performance of the nucleating agent is enhanced.

For example, regarding the phosphonic acid metal salt described in Patent Document 5, it is described that pulverization treatment or the like is carried out where appropriate so as to achieve an average particle diameter of not larger than 10 μm. It is also described in Example of the same document that a phosphonic acid metal salt with an average particle diameter of 1.1 μm at the smallest is produced.

RELATED ART DOCUMENTS

Patent Document

Patent Document 1: Japanese Patent Application Publication No. JP-A-8-3432
Patent Document 2: Japanese Patent Application Publication No. JP-A-10-87975
Patent Document 3: Japanese Patent Application Publication No. JP-A-10-158369
Patent Document 4: Japanese Patent Application Publication No. JP-A-2003-192883
Patent Document 5: International Publication No. WO 2005/097894 pamphlet
Patent Document 6: Japanese Patent Application Publication No. JP-A-2008-156616

DISCLOSURE OF THE INVENTION

Problem to be Solved by the Invention

As described above, various nucleating agents have been developed for enhancing the crystallization rate and the degree of crystallinity of a polylactic acid resin and, in recent years, a further effective nucleating agent is desired to be developed that can yield a polylactic acid resin with greater molding processability and heat resistance. For this purpose, the size of the nucleating agent is required to be further smaller. However, the size of a particle obtained by the above methods is of the order of several micrometers and is larger than 1 μm at the smallest, and some effort is required including pulverization treatment for achieving this small size.

An object of the present invention is to develop a new method that can produce, with higher efficiently, a particle with a further smaller particle diameter of, for example, not larger than 0.5 μm without requiring pulverization treatment or a similar process.

Means for Solving the Problem

The inventors of the present invention have conducted intensive research in order to solve these problems and, as a result, found that, in producing a phosphonic acid metal salt of a smaller size to be used as a nucleating agent, a base can be added to the reaction system to adjust the pH range of the system to be neutral to basic in order to obtain (precipitate) a metal salt of a smaller particle size and, in addition, water serving as a reaction medium can be removed immediately after the precipitation of the metal salt in order to prevent an increase in the particle diameter of the product, thereby maintaining the smaller particle size. Thus, they have now completed the present invention.

Namely, the present invention provides:

as a first aspect, a method for producing phosphonic acid metal salt fine particles including the steps of:

a) causing a reaction of a phosphonic acid compound of Formula (I):

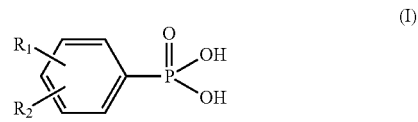

(where $R_1$ and $R_2$ are each independently a hydrogen atom, an alkyl group having 1 to 10 carbon atoms, or an alkoxycarbonyl group having 1 to 10 carbon atoms) with a base in an aqueous medium to adjust the pH range of the reaction system to be neutral to basic;

b) causing a reaction of the product obtained in the step a) with a metal salt to precipitate a phosphonic acid metal salt from the aqueous medium;

c) removing water from the phosphonic acid metal salt precipitated in the step b); and d) heating and drying the phosphonic acid metal salt from which water is removed in the step c).

As a second aspect, in the method for producing phosphonic acid metal salt fine particles according to the first aspect, the phosphonic acid metal salt is one, two, or more metal salts selected from a group consisting of lithium salts, sodium salts, potassium salts, magnesium salts, calcium salts, barium salts, iron salts, cobalt salts, copper salts, manganese salts, and zinc salts.

As a third aspect, in the method for producing phosphonic acid metal salt fine particles according to the first aspect or the second aspect, in the step a) of adjusting the pH range of the reaction system to be neutral to basic, the reaction system is adjusted to be pH 7 to 14.

As a fourth aspect, in the method for producing phosphonic acid metal salt fine particles according to any one of the first aspect to the third aspect, the step b) of precipitating a phosphonic acid metal salt from the aqueous medium is performed by adding the product obtained in the step a) dropwise to an aqueous solution of the metal salt.

As a fifth aspect, in the method for producing phosphonic acid metal salt fine particles according to any one of the first aspect to the fourth aspect, the step c) of removing water from the precipitated phosphonic acid metal salt is performed by substituting water that is a reaction medium with an organic solvent.

As a sixth aspect, in the method for producing phosphonic acid metal salt fine particles according to the fifth aspect, the organic solvent is a water soluble organic solvent with a boiling point of 120° C. or less.

As a seventh aspect, in the method for producing phosphonic acid metal salt fine particles according to the sixth aspect, the organic solvent is methanol, ethanol, or acetone.

As an eighth aspect, in the method for producing phosphonic acid metal salt fine particles according to any one of the first aspect to the seventh aspect, the step c) of removing water from the precipitated phosphonic acid metal salt is performed by drying under reduced pressure at 5 to 70° C.

As a ninth aspect, a phosphonic acid metal salt fine particle is obtained by the method as described in any one of the first aspect to the eighth aspect, in which an average particle diameter of the particle is 0.01 to 0.5 μm.

As a tenth aspect, a polylactic acid resin composition contains 0.01 to 10 parts by mass of the phosphonic acid metal salt fine particle as described in the ninth aspect relative to 100 parts by mass of a polylactic acid resin.

Effects of the Invention

According to the present invention, by initially adding a base to the reaction system to adjust the pH range of the system to be neutral to basic, specifically by first causing a reaction of a phosphonic acid compound with a base in an aqueous medium to adjust the pH range of the reaction system to be 7 to 14 and then causing a reaction of the obtained product with a metal salt that is a metal source, a phosphonic acid metal salt with an average particle diameter of not larger than 0.5 μm can be precipitated in a reaction medium (the aqueous medium). In addition, by removing as much water serving as the reaction medium, as possible by means of solvent substitution or the like before heating and drying, the product (phosphonic acid metal salt) can be prevented from being redissolved and from being recrystallized during heating and drying and therefore the particle diameter can be prevented from increasing, whereby a phosphonic acid metal salt fine particle with an average particle diameter of not larger than 0.5 μm can be obtained.

Thus, the production method of the present invention can produce a phosphonic acid metal salt fine particle with a smaller average particle diameter than that in conventional production methods without requiring additional steps including pulverization.

The fine particle obtained in the present invention has a very small particle diameter compared to that of a phosphonic acid metal salt particle with an average particle diameter of several micrometers obtained in an ordinary production method. For this reason, when the phosphonic acid metal salt fine particle obtained in the production method of the present invention is used as a nucleating agent in production of a polyester resin including a polylactic acid resin, a crystalline polyolefin resin, or the like, the transparency and an effect of facilitating crystallization of the resin can be enhanced.

BEST MODES FOR CARRYING OUT THE INVENTION

Figure 1:
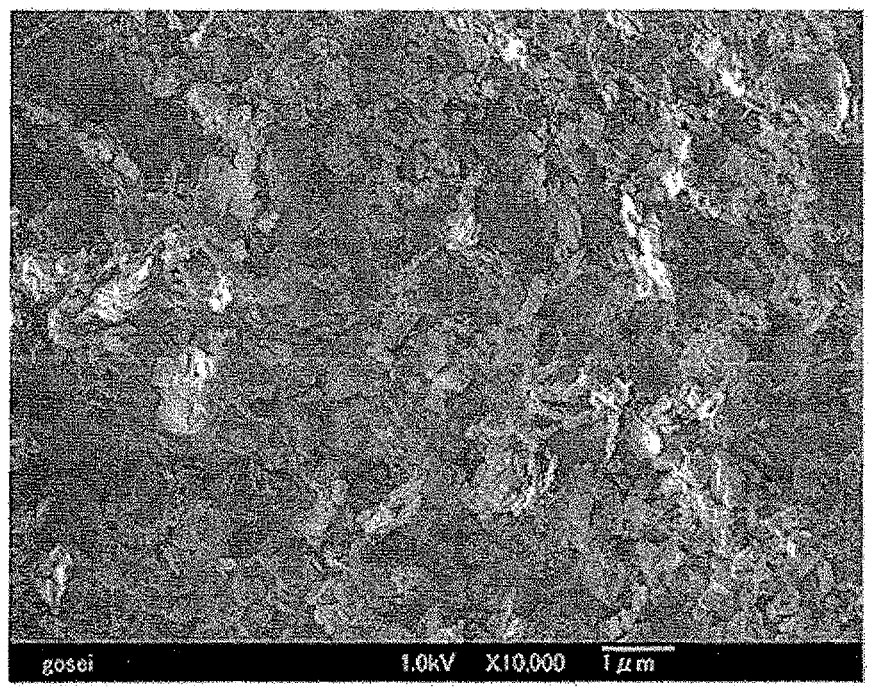
FIG. 1 is a scanning electron microscope (SEM) image of a phosphonic acid zinc salt produced in Example 1.

The present invention provides a production method characterized by including a) causing a reaction of a phosphonic acid compound with a base in an aqueous medium to adjust the pH range of the reaction system to be neutral to basic, b)

causing a reaction of the product obtained in the step a) with a metal salt to precipitate a phosphonic acid metal salt from the aqueous medium, c) removing water from the phosphonic acid metal salt precipitated in the step b), and d) heating and drying the phosphonic acid metal salt from which water is removed in the step e).

Even when addition of a base is performed after the reaction of the phosphonic acid compound with the metal salt or even when no base is added, a crystal of a phosphonic acid metal salt can be precipitated. However, the size of a particle obtained is at least 500 nm or larger because a reaction liquid becomes acidic during the course of the reaction. It is considered that, when the reaction liquid becomes acidic during the course of the reaction, the solubility of a phosphonic acid metal salt particle precipitated increases to cause the phosphonic acid metal salt particle to dissolve in the reaction liquid (the aqueous medium) and the metal salt to recrystallize, and therefore an equilibrium reaction between the dissolution and the recrystallization leads to an increase in the particle size.

When an abundance of water serving as a reaction medium, remains during heating and drying after the phosphonic acid metal salt that is precipitated from the aqueous medium, the phosphonic acid metal salt dissolves in the remaining water and therefore an equilibrium reaction between the dissolution and the recrystallization of the metal salt leads to an increase in the particle size, in a like manner.

To deal with these particle size increases that happen in various instances, the inventors of the present invention causes a reaction of a phosphonic acid compound that is to be subjected to a reaction with a metal salt, with a base in an aqueous medium to adjust the pH range of the reaction system in order to maintain the pH of the reaction system to be weakly acidic to basic even after the precipitation of a phosphonic acid metal salt, and further removes as much water serving as a reaction medium, as possible from the precipitated phosphonic acid metal salt before heating and drying. Thus, an equilibrium reaction between the recrystallization and the dissolution of the phosphonic acid metal salt in a reaction liquid (the aqueous medium) during the precipitation of the phosphonic acid metal salt and in the remaining water during drying can be prevented and, in turn, an increase in the particle size of the metal salt can be prevented.

The present invention will be described in detail.

The step a) of causing a reaction of a phosphonic acid compound with a base in an aqueous medium to adjust the pH range of the reaction system to be neutral to basic The phosphonic acid compound used in the present invention is a compound of Formula (I).

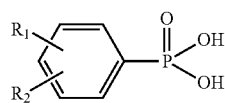

In the phosphonic acid compound of Formula (I), $R_1$ and $R_2$ each is a hydrogen atom, an alkyl group having 1 to 10 carbon atoms such as a methyl group, an ethyl group, an n-propyl group, an isopropyl group, an n-butyl group, an isobutyl group, and a tert-butyl group, or an alkoxycarbonyl group having 1 to 10 carbon atoms such as a methoxycarbonyl group and an ethoxycarbonyl group. $R_1$ and $R_2$ may be the same or different from each other.

Specific examples of the phosphonic acid compounds of Formula (I) include phenylphosphonic acid, 4-methylphenylphosphonic acid, 4-ethylphenylphosphonic acid, 4-n-propylphenylphosphonic acid, 4-isopropylphenylphosphonic acid, 4-n-butylphenylphosphonic acid, 4-isobutylphenylphosphonic acid, 4-tert-butylphenylphosphonic acid, 3,5-dimethoxycarbonylphenylphosphonic acid, 3,5-diethoxycarbonylphenylphosphonic acid, 2,5-dimethoxycarbonylphenylphosphonic acid, 2,5-diethoxycarbonylphenylphosphonic acid, and the like.

In the present invention, by causing a reaction of the phosphonic acid compound of Formula (I) with a base in an aqueous medium to adjust, beforehand, the pH range of the reaction system to be neutral to basic, specifically pH 7 to 14 or pH 7 to 11, the pH range of the reaction system can be maintained to be weakly acidic to basic even after the step b) (of precipitating a phosphonic acid metal salt) to be described below.

The base to be subjected to a reaction with the phosphonic acid compound is not particularly limited and, for example, sodium hydroxide, sodium carbonate, sodium hydrogen carbonate, or the like can be used.

Specifically, this step is carried out by, for example, mixing an aqueous solution of the phosphonic acid compound of Formula (I) with an aqueous solution of the base.

The step b) of causing a reaction of the product obtained in the step a) with a metal salt to precipitate a phosphonic acid metal salt from the aqueous medium In this step, the reaction of the product obtained in the step a) (a solution containing the phosphonic acid compound) with a metal salt is performed by, for example, mixing the product with an aqueous solution containing the metal salt. The reaction is preferably performed by adding the product dropwise to the aqueous solution containing the metal salt.

Therefore, the metal salt serving as a metal source, used in this step is preferably a water soluble salt.

The salt is not particularly limited provided that the salt is water soluble, and examples of the salts that can be used include sulfates, nitrates, chlorides, carbonates, acetates, and the like and preferably chlorides and acetates.

As the metal used herein, a monovalent, divalent, or trivalent metal can be used. Two or more of the metal can be used as a mixture. Specific examples of the metal salts include lithium salts, sodium salts, potassium salts, magnesium salts, aluminum salts, calcium salts, barium salts, manganese salts, iron salts, cobalt salts, nickel salts, copper salts, zinc salts, and the like. Among these, lithium salts, sodium salts, potassium salts, magnesium salts, calcium salts, barium salts, iron salts, cobalt salts, copper salts, manganese salts, and zinc salts are preferable and zinc salts are particularly preferable.

The temperature at which the product obtained in the step a) (a solution containing the phosphonic acid compound) is subjected to a reaction with the aqueous solution containing the metal salt can affect the particle diameter of a phosphonic acid metal salt fine particle to be obtained later. In other words, a higher reaction temperature results in an increase in the solubility of a phosphonic acid metal salt to be precipitated, which leads to recrystallization to increase the particle size. Therefore, to achieve a purpose of the present invention, namely to obtain a fine particle, the reaction temperature is preferably maintained at 30° C. or less.

The step c) of removing water from the phosphonic acid metal salt precipitated in the step b)

This step is preferably carried out by (i) substitution of water serving as a reaction medium, with an organic solvent or (ii) drying under reduced pressure. However, this step is not particularly limited to that.

Although not being particularly limited, the organic solvent used in (i) is preferably a water soluble organic solvent for efficient removal of water and is further preferably an organic solvent with a boiling point of lower than about 120° C. for easy drying.

Examples of the organic solvents include methanol, ethanol, acetone, 1-propanol, 2-propanol, tert-butanol, 1,2-dimethoxyethane, tetrahydrofuran, 1,4-dioxane, acetonitrile, and the like, and methanol, ethanol, and acetone are preferable among them.

In (i), specifically, a reaction liquid (suspension) in which the phosphonic acid metal salt precipitates in the previous step is filtrated, and the residue is then redispersed in the organic solvent, followed by refiltration. Preferably redispersion in the organic solvent and refiltration are repeated so as to substitute as much water as possible with the organic solvent.

The residue may be washed with water several times before redispersion in the organic solvent.

The temperature during drying under reduced pressure in (ii) is preferably low so as not to affect the particle diameter of the phosphonic acid metal salt fine particle. Considering an efficiency of distilling water off, the drying under reduced pressure is preferably carried out at 5 to 70° C. and more preferably at 30 to 50° C.

The pressure during drying under reduced pressure is not particularly limited provided that the pressure allows drying at the temperature, and the drying under reduced pressure is carried out at 1 to 5 kPa for 12 to 60 hours, for example.

The step d) of heating and drying the phosphonic acid metal salt from which water is removed in the step c)

After water is removed from the phosphonic acid metal salt in the step c), a phosphonic acid metal salt fine particle that is the final product, is obtained by heating and drying.

The temperature during heating is preferably 100 to 300° C. Temperatures higher than 300° C. are not preferable because the decomposition of the phosphonic acid metal salt can be induced, and temperatures lower than 100° C. are not preferable because the phosphonic acid metal salt exists as a hydrate (a monohydrate in the case of zinc phenylphosphonate or calcium phenylphosphonate to be described below, for example), which means the salt is not suitable as a nucleating agent for a resin that is not resistant to hydrolysis (a polyester resin, for example).

The average particle diameter (average particle size) of the phosphonic acid metal salt fine particle of the present invention obtained by these steps is 0.05 to 0.5 μm and is preferably 0.05 to 0.3 μm.

The shape of the phosphonic acid metal salt fine particle of the present invention can be granular or disc-like (see FIG. 1 to FIG. 7 to be described below) or rectangular (a strip, see FIG. 11 to FIG. 13 to be described below) depending on, for example, the species of the metal salt. In the case of a rectangular particle, the "average particle diameter" in the present invention means the average of approximately longest shorter diameters (minor axes) of the rectangular particles. The dimensions of the rectangular particle are described by the length (longer diameter), the width (shorter diameter), and the thickness and these numerical value's satisfy the condition<longer diameter≧shorter diameter≧thickness>.

The present invention also relates to a polylactic acid resin composition containing 0.01 to 10 parts by mass of the phosphonic acid metal salt fine particle with an average particle diameter of 0.05 to 0.5 μm, as described above, relative to 100 parts by mass of a polylactic acid resin.

EXAMPLES

The present invention will be described more specifically by examples. The present invention is, however, not limited to these examples. In the following examples, a twin pH meter manufactured by HORIBA, Ltd. is used in pH measurements.

Example 1

A solution obtained by mixing a 15% by mass aqueous phenylphosphonic acid solution (7.9 g of phenylphosphonic acid and 44.8 g of water) and a 15% by mass aqueous sodium hydroxide solution (4.0 g of sodium hydroxide and 22.7 g of water) to adjust the mixed solution to be pH 8.8 was added dropwise to a 6% by mass aqueous zinc chloride solution (6.8 g of zinc chloride and 100.0 g of water, pH 5.6) with stirring to precipitate zinc phenylphosphonate. The suspension had a pH of 8.8.

The obtained suspension was filtrated, and the obtained residue (wet matter) was then redispersed in 300 mL of water, followed by refiltration. These were repeated twice. The residue (wet matter) was then redispersed in 300 mL of methanol, followed by refiltration. These were repeated twice. Lastly the resultant was dried under reduced pressure at 20° C. to distill off methanol and was then dried at 120° C. for 6 hours.

An SEM (scanning electron microscope) image of the obtained dry matter (powder) is shown in FIG. 1.

Example 2

A solution obtained by mixing a 15% by mass aqueous phenylphosphonic acid solution (7.2 g of phenylphosphonic acid and 40.8 g of water) and a 15% by mass aqueous sodium hydroxide solution (3.7 g of sodium hydroxide and 20.7 g of water) to adjust the mixed solution to be pH 8.8 was added dropwise to an 8% by mass aqueous zinc acetate solution (10.0 g of zinc acetate dihydrate and 90.0 g of water, pH 6.1) with stirring to precipitate zinc phenylphosphonate. The suspension had a pH of 6.2.

The obtained suspension was filtrated, and the obtained residue (wet matter) was then redispersed in 300 mL of water, followed by refiltration. These were repeated twice. The residue (wet matter) was then redispersed in 300 mL of acetone, followed by refiltration. These were repeated twice. Lastly the resultant was dried under reduced pressure at 20° C. to distill off acetone and was then dried at 120° C. for 6 hours.

Figure 2:
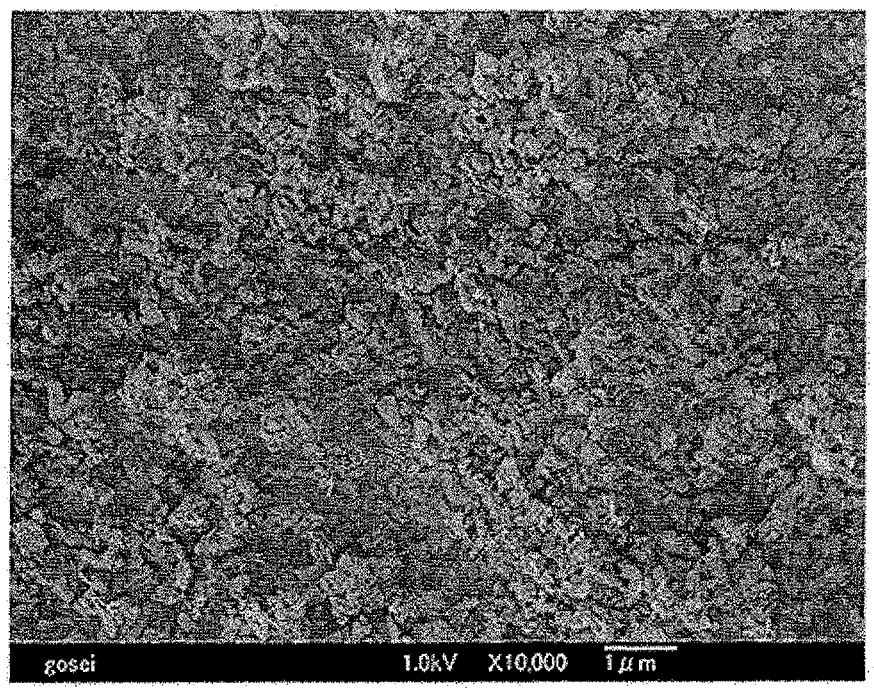
FIG. 2 is a scanning electron microscope (SEM) image of a phosphonic acid zinc salt produced in Example 2.

An SEM image of the obtained dry matter (powder) is shown in FIG. 2.

Example 3

A solution obtained by mixing a 15% by mass aqueous phenylphosphonic acid solution (7.9 g of phenylphosphonic acid and 44.8 g of water) and a 15% by mass aqueous sodium hydroxide solution (4.0 g of sodium hydroxide and 22.7 g of water) to adjust the mixed solution to be pH 8.8 was added dropwise to a 6% by mass aqueous zinc chloride solution (6.8 g of zinc chloride and 100.0 g of water, pH 5.6) with stirring to precipitate zinc phenylphosphonate. The suspension had a pH of 8.8.

The obtained suspension was filtrated, and the obtained residue (wet matter) was then redispersed in 300 mL of water, followed by refiltration. These were repeated twice. The residue (wet matter) was then redispersed in 300 mL of ethanol, followed by refiltration. These were repeated twice. Lastly the resultant was dried under reduced pressure at 20° C. to distill off ethanol and was then dried at 120° C. for 6 hours.

Figure 3:
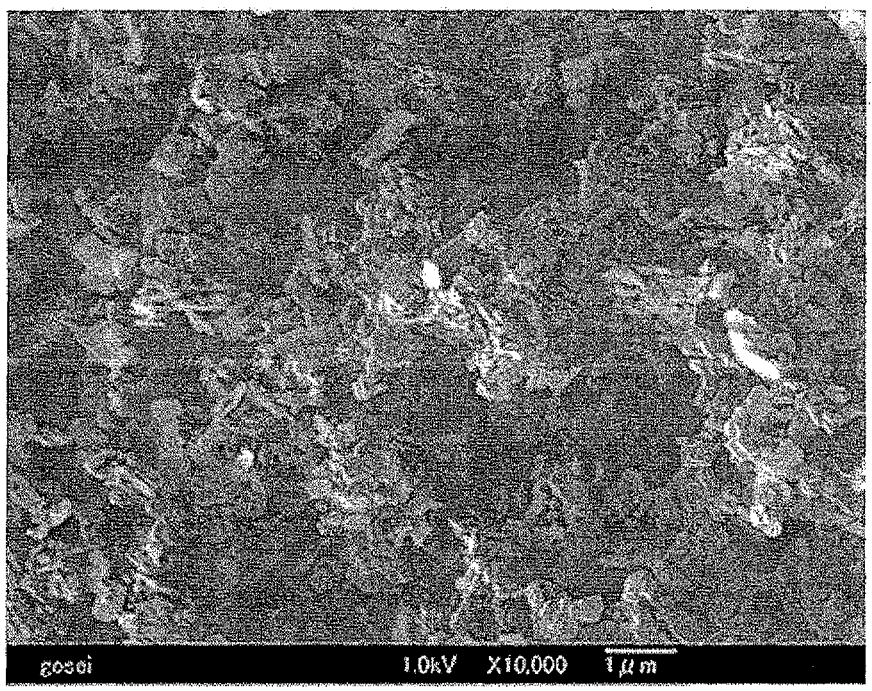
FIG. 3 is a scanning electron microscope (SEM) image of a phosphonic acid zinc salt produced in Example 3.

An SEM image of the obtained dry matter (powder) is shown in FIG. 3.

Example 4

A solution obtained by mixing a 15% by mass aqueous phenylphosphonic acid solution (7.2 g of phenylphosphonic acid and 40.8 g of water) and a 15% by mass aqueous sodium hydroxide solution (3.7 g of sodium hydroxide and 20.7 g of water) to adjust the mixed solution to be pH 8.8 was added dropwise to a 7% by mass aqueous zinc chloride solution (6.3 g of zinc chloride and 90.0 g of water, pH 5.6) with stirring to precipitate zinc phenylphosphonate. The suspension had a pH of 8.8.

The obtained suspension was filtrated, and the obtained residue (wet matter) was then redispersed in 300 mL of water, followed by refiltration. These were repeated twice. The residue (wet matter) was then redispersed in 300 mL of acetone, followed by refiltration. These were repeated twice. Lastly the resultant was dried under reduced pressure at 20° C. to distill off acetone and was then dried at 120° C. for 6 hours.

Figure 4:
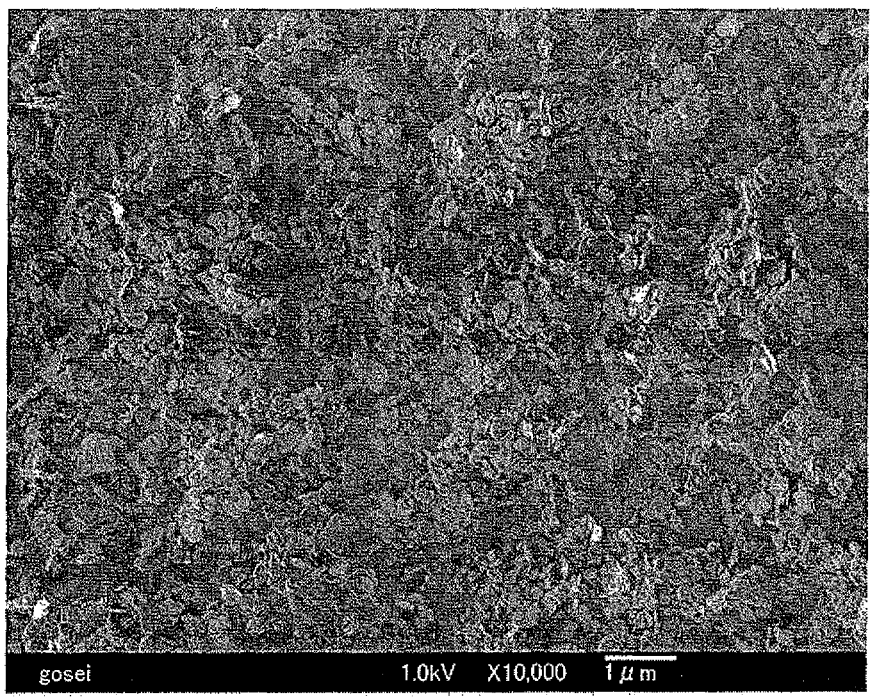
FIG. 4 is a scanning electron microscope (SEM) image of a phosphonic acid zinc salt produced in Example 4.

An SEM image of the obtained dry matter (powder) is shown in FIG. 4.

Example 5

A solution obtained by mixing a 15% by mass aqueous phenylphosphonic acid solution (7.2 g of phenylphosphonic acid and 40.8 g of water) and a 15% by mass aqueous sodium hydroxide solution (3.7 g of sodium hydroxide and 20.7 g of water) to adjust the mixed solution to be pH 8.8 was added dropwise to a 6% by mass aqueous zinc chloride solution (6.3 g of zinc chloride and 100.0 g of water, pH 5.6) with stirring to precipitate zinc phenylphosphonate. The suspension had a pH of 8.8.

The obtained suspension was filtrated, and the obtained residue (wet matter) was then redispersed in 300 mL of water, followed by refiltration. These were repeated twice. The resultant was then dried under reduced pressure at 40° C. for 12 hours to distill off water and was then dried at 120° C. for 6 hours. The end point of the drying under reduced pressure was ensured by thermogravimetric analyses (Thermo Plus manufactured by Rigaku Corporation, temperature raising rate: 10° C./minute) of dry matter to confirm that the weight loss due to moisture evaporation was equivalent to the amount of the water of crystallization.

Figure 5:
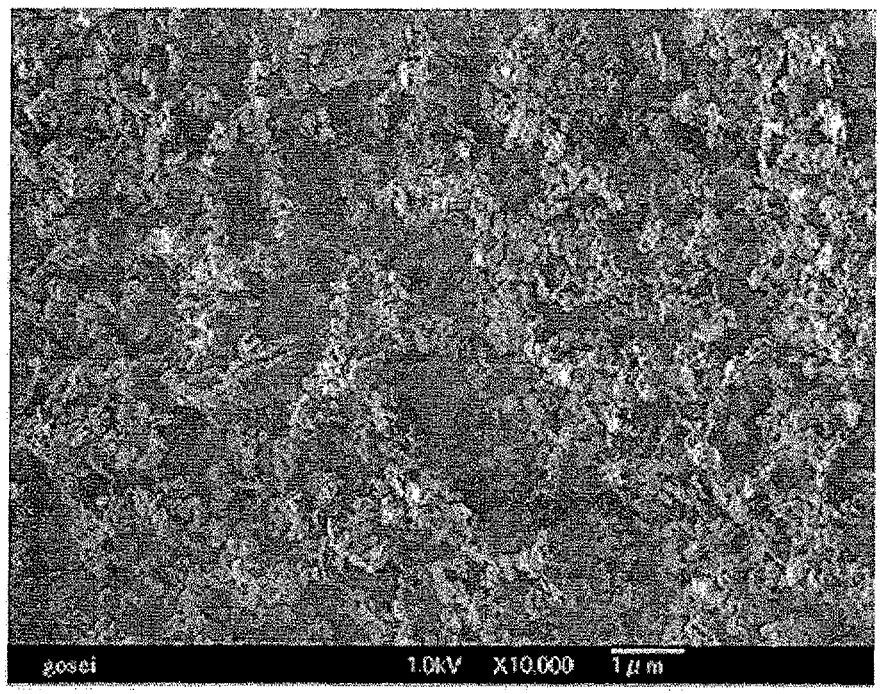
FIG. 5 is a scanning electron microscope (SEM) image of a phosphonic acid zinc salt produced in Example 5.

An SEM image of the obtained dry matter (powder) is shown in FIG. 5.

Example 6

The same process as in Example 5 was performed except that the temperature during drying under reduced pressure was changed to 50° C.

Figure 6:
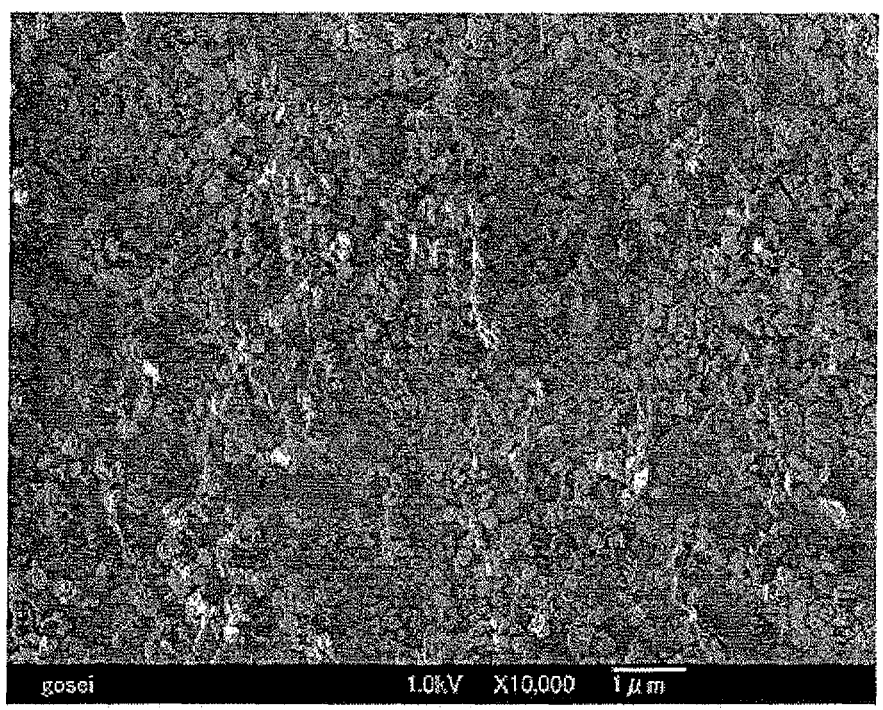
FIG. 6 is a scanning electron microscope (SEM) image of a phosphonic acid zinc salt produced in Example 6.

An SEM image of the obtained dry matter (powder) is shown in FIG. 6.

Example 7

The same process as in Example 5 was performed except that the temperature during drying under reduced pressure was changed to 60° C.

Figure 7:
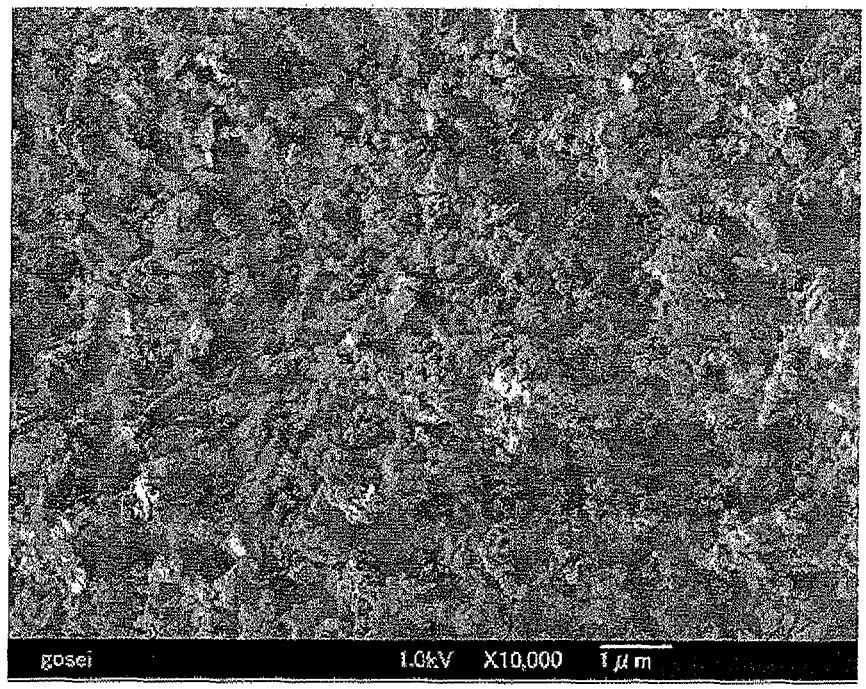
FIG. 7 is a scanning electron microscope (SEM) image of a phosphonic acid zinc salt produced in Example 7.

An SEM image of the obtained dry matter (powder) is shown in FIG. 7.

Comparative Example 1

A solution obtained by mixing a 15% by mass aqueous phenylphosphonic acid solution (7.2 g of phenylphosphonic acid and 40.8 g of water) and a 15% by mass aqueous sodium hydroxide solution (3.7 g of sodium hydroxide and 20.7 g of water) to adjust the mixed solution to be pH 8.8 was added dropwise to an 8% by mass aqueous zinc acetate solution (10.0 g of zinc acetate dihydrate and 90.0 g of water, pH 6.1) with stirring to precipitate zinc phenylphosphonate. The suspension had a pH of 6.3.

The obtained suspension was filtrated, and the obtained residue (wet matter) was then redispersed in 300 mL of water, followed by refiltration. These were repeated twice. Subsequently, the resultant was dried at 120° C. for 12 hours.

Figure 8:
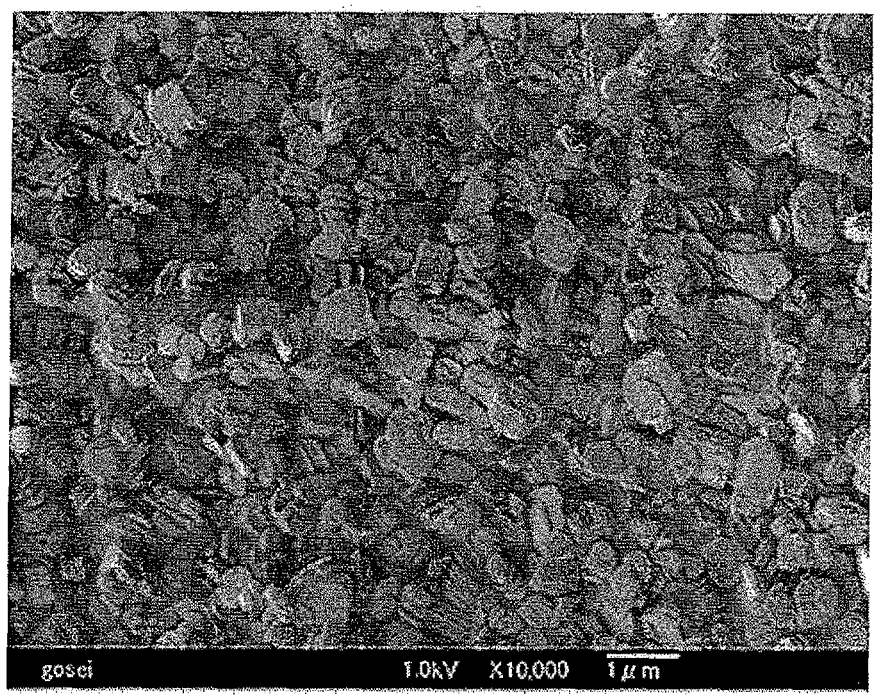
FIG. 8 is a scanning electron microscope (SEM) image of a phosphonic acid zinc salt produced in Comparative Example 1.

An SEM image of the obtained dry matter (powder) is shown in FIG. 8.

Comparative Example 2

To an 8% by mass aqueous zinc acetate solution (10.0 g of zinc acetate dihydrate and 90.0 g of water, pH 6.3), a 15% by mass aqueous phenylphosphonic acid solution (7.2 g of phenylphosphonic acid and 40.8 g of water, pH 0.5) was added dropwise with stirring to precipitate zinc phenylphosphonate. The suspension had a pH of 3.1.

The obtained suspension was filtrated, and the obtained residue (wet matter) was then redispersed in 300 mL of water, followed by refiltration. These were repeated twice. The residue (wet matter) was then redispersed in 300 mL of acetone, followed by refiltration. These were repeated twice. Lastly the resultant was dried under reduced pressure at 20° C. to distill off acetone and was then dried at 120° C. for 12 hours.

Figure 9:
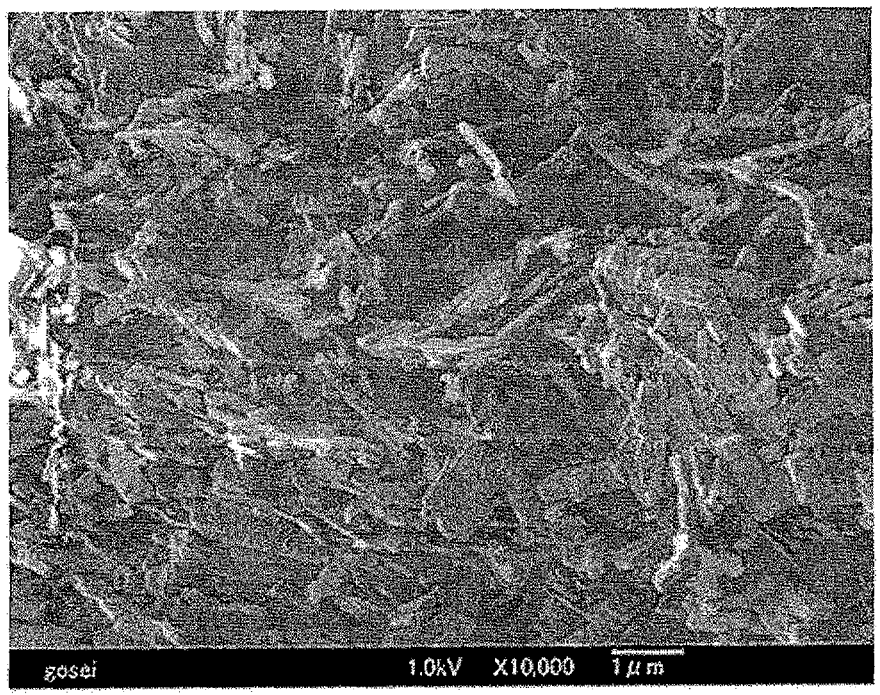
FIG. 9 is a scanning electron microscope (SEM) image of a phosphonic acid zinc salt produced in Comparative Example 2.

An SEM image of the obtained dry matter (powder) is shown in FIG. 9.

Comparative Example 3

To an 8% by mass aqueous zinc acetate solution (10.0 g of zinc acetate dihydrate and 90.0 g of water, pH 6.3), a 15% by mass aqueous phenylphosphonic acid solution (7.2 g of phenylphosphonic acid and 40.8 g of water, pH 0.5) was added dropwise with stirring to precipitate zinc phenylphosphonate. The suspension had a pH of 2.8. Subsequently, a 15% by mass aqueous sodium hydroxide solution (3.7 g of sodium hydroxide and 20.7 g of water) was added dropwise thereto with stirring to adjust the pH to be 6.8.

The obtained suspension was filtrated, and the obtained residue (wet matter) was then redispersed in 300 mL of water, followed by refiltration. These were repeated twice. The residue (wet matter) was then redispersed in 300 mL of acetone, followed by refiltration. These were repeated twice. Lastly the resultant was dried under reduced pressure at 20° C. to distill off acetone and was then dried at 120° C. for 12 hours.

Figure 10:
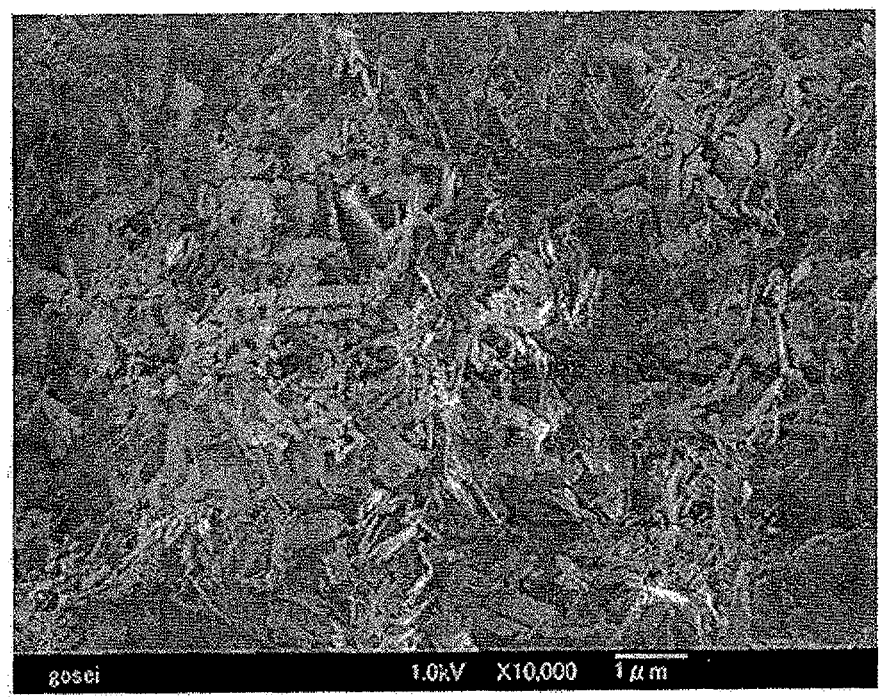
FIG. 10 is a scanning electron microscope (SEM) image of a phosphonic acid zinc salt produced in Comparative Example 3.

An SEM image of the obtained dry matter (powder) is shown in FIG. 10.

In each of Example 1 to Example 7 and Comparative Example 1 to Comparative Example 3, a reaction liquid obtained 30 minutes after zinc phenylphosphonate precipitated (in Comparative Example 3, after neutralized with an aqueous sodium hydroxide solution) was recovered, and the average particle diameter of zinc phenylphosphonate in the reaction liquid was measured. The average particle diameter was determined by charging the reaction liquid in a laser diffraction particle size distribution analyzer (manufactured by Malvern Instruments Ltd. "MasterSizer 2000") and then measuring particle diameter every 1 minute at 1,500 rpm and at an ultrasound level of 100 in the analyzer. The minimum value obtained was used. The average particle diameter herein refers to a d50 value (a median diameter), derived from the Mie theory, of the particle in dispersion medium.

The average particle diameter of a zinc phenylphosphonate powder particle after drying was obtained by randomly sampling 50 particles in an SEM (scanning electron microscope)

image of dry matter to determine the average length in the major axis direction of the particles. The results obtained are shown in Table 1.

TABLE 1

| | Metal source | Timing of base addition* | Washing solvent | Average particle diameter (μm) | |
|---|---|---|---|---|---|
| | | | | In reaction liquid | Dry matter |
| Ex. 1 | Zinc chloride | PPA was initially neutralized | Water → methanol | 0.19 | 0.24 |
| Ex. 2 | Zinc acetate | PPA was initially neutralized | Water → acetone | 0.17 | 0.16 |
| Ex. 3 | Zinc chloride | PPA was initially neutralized | Water → ethanol | 0.23 | 0.19 |
| Ex. 4 | Zinc chloride | PPA was initially neutralized | Water → acetone | 0.16 | 0.17 |
| Ex. 5 | Zinc chloride | PPA was initially neutralized | Water (→ dried under reduced pressure at 40° C.) | 0.15 | 0.18 |
| Ex. 6 | Zinc chloride | PPA was initially neutralized | Water (→ dried under reduced pressure at 50° C.) | 0.14 | 0.14 |
| Ex. 7 | Zinc chloride | PPA was initially neutralized | Water (→ dried under reduced pressure at 60° C.) | 0.14 | 0.23 |
| Comp. Ex. 1 | Zinc acetate | PPA was initially neutralized | Water alone | 0.17 | 0.54 |
| Comp. Ex. 2 | Zinc acetate | No base used | Water → acetone | 4.77 | 0.76 |
| Comp. Ex. 3 | Zinc acetate | Added after salt precipitation | Water → acetone | 7.48 | 0.52 |

*PPA: phenylphosphonic acid

As shown in Table 1, the procedures of Example 1 to Example 7 each achieved an average particle diameter of 0.14 to 0.24 μm, even after drying, of a zinc phenylphosphonate fine particle.

On the other hand, in Comparative Example 1 where water alone was used as a washing solvent and no organic solvent substitution was performed, zinc phenylphosphonate at the time of precipitation was a fine particle, which grew to 0.54 μm after drying.

In each of Comparative Example 2 where no base was used and Comparative Example 3 where a base was used after salt precipitation, the particle diameter greatly increased in the reaction liquid and exceeded 0.5 μm after drying.

Example 8 and Comparative Example 4

Evaluation of Crystallization Temperature and Crystallization Time

To 100 parts by mass of a polylactic acid resin (manufactured by Mitsui Chemicals, Inc.; trade name: LACEA-H100), 1 part by mass of zinc phenylphosphonate (dry matter) obtained in Example 4 or zinc phenylphosphonate manufactured by Nissan Chemical Industries, Ltd. (trade name: ECOPROMOTE, average particle diameter: 2 to 3 μm) was added, followed by melt kneading at 185° C. for 5 minutes using a Labo Plastomill manufactured by Toyo Seiki Seisaku-sho, Ltd.

Subsequently, each sample was evaluated for a crystallization temperature and a crystallization time on a differential scanning calorimeter (DSC) "Diamond DSC" manufactured by PerkinElmer, Inc. in the following procedures. The results obtained are shown in Table 2.

1) Crystallization temperature: the temperature of approximately 5 mg of a sample was raised at 10° C./minute to 200° C., which was maintained for 5 minutes to allow melt to proceed, and the resultant was cooled to 30° C. at 5° C./minute. The temperature at which a peak was reached by an exotherm due to crystallization of a polylactic acid resin during cooling was used as a crystallization temperature.

2) Crystallization time: the temperature of approximately 5 mg of a sample was raised at 10° C./minute to 200° C., which was maintained for 5 minutes to allow melt to proceed. The resultant was rapidly cooled at 100° C./minute to 110° C., which was maintained. The time at which a peak was reached by an exotherm due to crystallization of a polylactic acid resin that was subsequently produced was used as a crystallization time.

TABLE 2

| | Zinc phenylphosphonate | Crystallization temperature (° C.) | Crystallization time (seconds) |
|---|---|---|---|
| Ex. 8 | Example 4 | 131.5 | 22 |
| Comp. Ex. 4 | ECOPROMOTE | 131.0 | 28 |

As shown in Table 2, zinc phenylphosphonate obtained in Example 4 had a higher crystallization temperature and a shorter induction period on isothermal crystallization compared to the zinc phenylphosphonate product (ECOPROMOTE), which confirms that the phosphonic acid metal salt fine particle has excellent performance as a nucleating agent.

Example 9

A solution obtained by mixing a 15% by mass aqueous phenylphosphonic acid solution (7.9 g of phenylphosphonic acid and 44.8 g of water) and a 15% by mass aqueous sodium hydroxide solution (4.0 g of sodium hydroxide and 22.7 g of water) to adjust the mixed solution to be pH 8.7 was added dropwise to an 8% by mass aqueous calcium chloride solution (7.4 g of calcium chloride dihydrate and 66.2 g of water) with stirring to precipitate calcium phenylphosphonate. The suspension had a pH of 7.1.

The obtained suspension was filtrated, and the obtained residue (wet matter) was then redispersed in 100 mL of water, followed by refiltration. These were repeated twice. The residue (wet matter) was then redispersed in 100 mL of acetone, followed by refiltration. These were repeated twice. Lastly the resultant was dried under reduced pressure at 20° C. to distill off acetone and was then dried at 200° C. for 12 hours.

Figure 11:
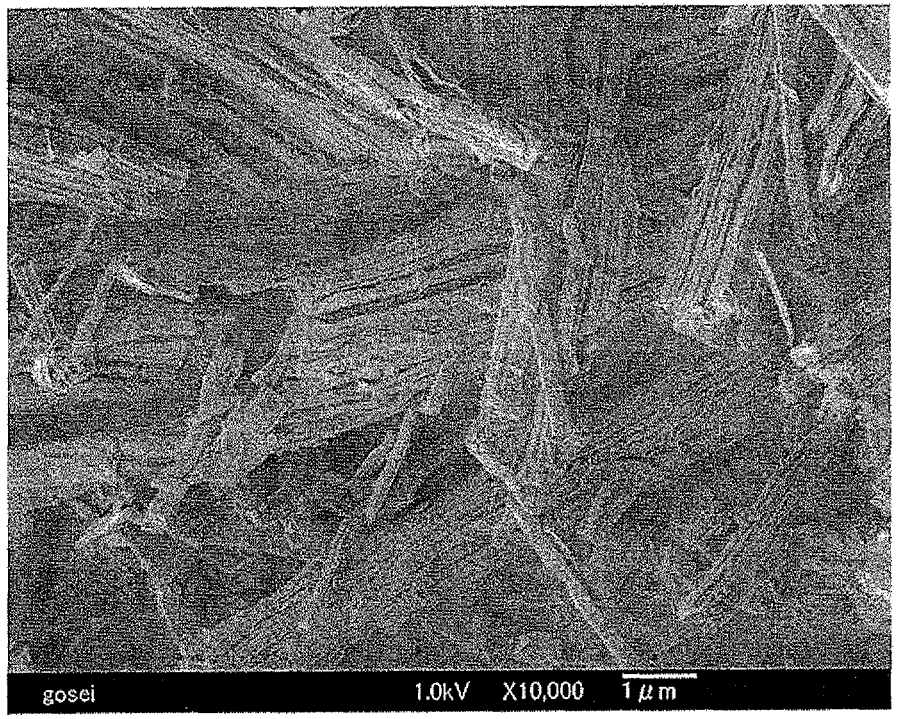
FIG. 11 is a scanning electron microscope (SEM) image of a phosphonic acid calcium salt produced in Example 9.

An SEM image of the obtained dry matter (powder) is shown in FIG. 11.

Example 10

A solution obtained by mixing a 15% by mass aqueous phenylphosphonic acid solution (7.9 g of phenylphosphonic acid and 44.9 g of water) and a 15% by mass aqueous sodium hydroxide solution (4.0 g of sodium hydroxide and 22.7 g of water) to adjust the mixed solution to be pH 9.4 was added dropwise to a 9% by mass aqueous calcium acetate solution (8.8 g of calcium acetate monohydrate and 79.3 g of water) with stirring to precipitate calcium phenylphosphonate. The suspension had a pH of 8.6.

The obtained suspension was filtrated, and the obtained residue (wet matter) was then redispersed in 100 mL of water, followed by refiltration. These were repeated twice. The residue (wet matter) was then redispersed in 100 mL of acetone, followed by refiltration. These were repeated twice. Lastly the resultant was dried under reduced pressure at 20° C. to distill off acetone and was then dried at 200° C. for 12 hours.

Figure 12:
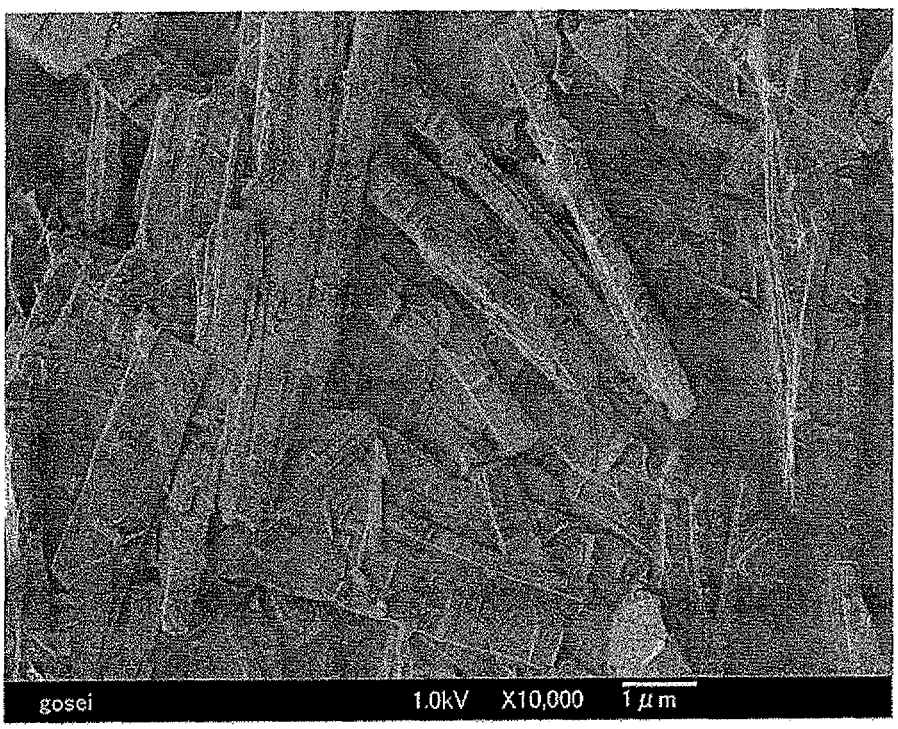
FIG. 12 is a scanning electron microscope (SEM) image of a phosphonic acid calcium salt produced in Example 10.

An SEM image of the obtained dry matter (powder) is shown in FIG. 12.

Example 11

A solution obtained by mixing a 15% by mass aqueous phenylphosphonic acid solution (7.9 g of phenylphosphonic acid and 44.9 g of water) and a 15% by mass aqueous sodium hydroxide solution (4.2 g of sodium hydroxide and 23.8 g of water) to adjust the mixed solution to be pH 12.4 was added dropwise to an 8% by mass aqueous calcium chloride solution (7.4 g of calcium chloride dihydrate and 66.2 g of water) with stirring to precipitate calcium phenylphosphonate. The suspension had a pH of 11.5.

The obtained suspension was filtrated, and the obtained residue (wet matter) was then redispersed in 100 mL of water, followed by refiltration. These were repeated twice. The resultant was then dried under reduced pressure at 40° C. for 12 hours to distill off water and was then dried at 200° C. for 12 hours. The end point of the drying under reduced pressure was ensured by thermogravimetric analyses (Thermo Plus manufactured by Rigaku Corporation, temperature raising rate: 10° C./minute) of dry matter to confirm that the weight loss due to moisture evaporation was equivalent to the amount of the water of crystallization.

Figure 13:
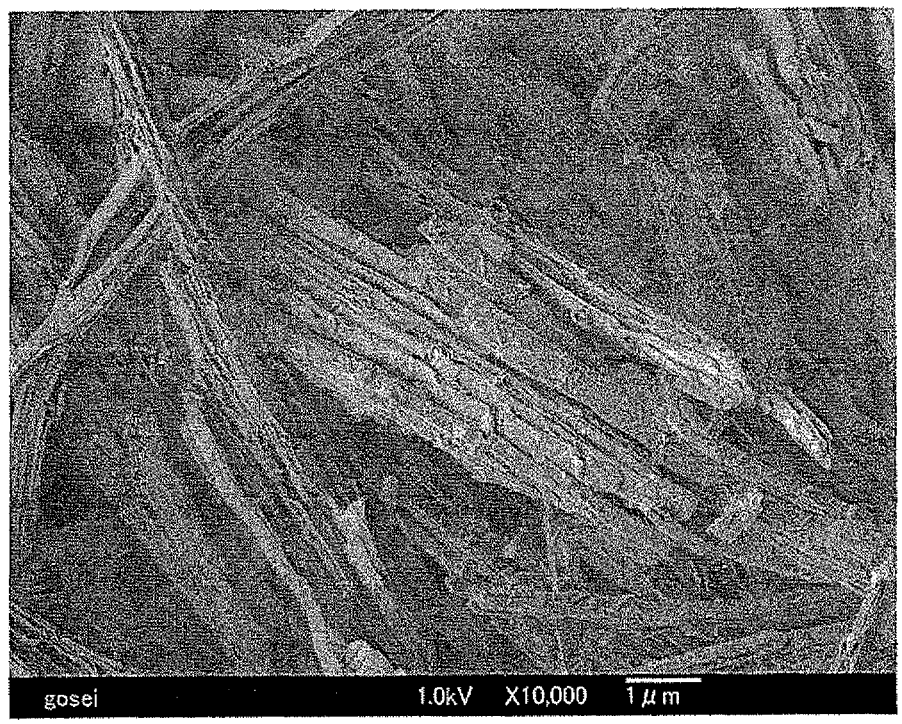
FIG. 13 is a scanning electron microscope (SEM) image of a phosphonic acid calcium salt produced in Example 11.

An SEM image of the obtained dry matter (powder) is shown in FIG. 13.

Comparative Example 5

A solution obtained by mixing a 15% by mass aqueous phenylphosphonic acid solution (7.9 g of phenylphosphonic acid and 44.9 g of water) and a 15% by mass aqueous sodium hydroxide solution (4.0 g of sodium hydroxide and 22.7 g of water) to adjust the mixed solution to be pH 9.4 was added dropwise to a 9% by mass aqueous calcium acetate solution (8.8 g of calcium acetate monohydrate and 79.3 g of water) with stirring to precipitate calcium phenylphosphonate. The suspension had a pH of 8.6.

The obtained suspension was filtrated, and the obtained residue (wet matter) was then redispersed in 100 mL of water, followed by refiltration. These were repeated twice. Subsequently, the resultant was dried at 200° C. for 12 hours.

Figure 14:
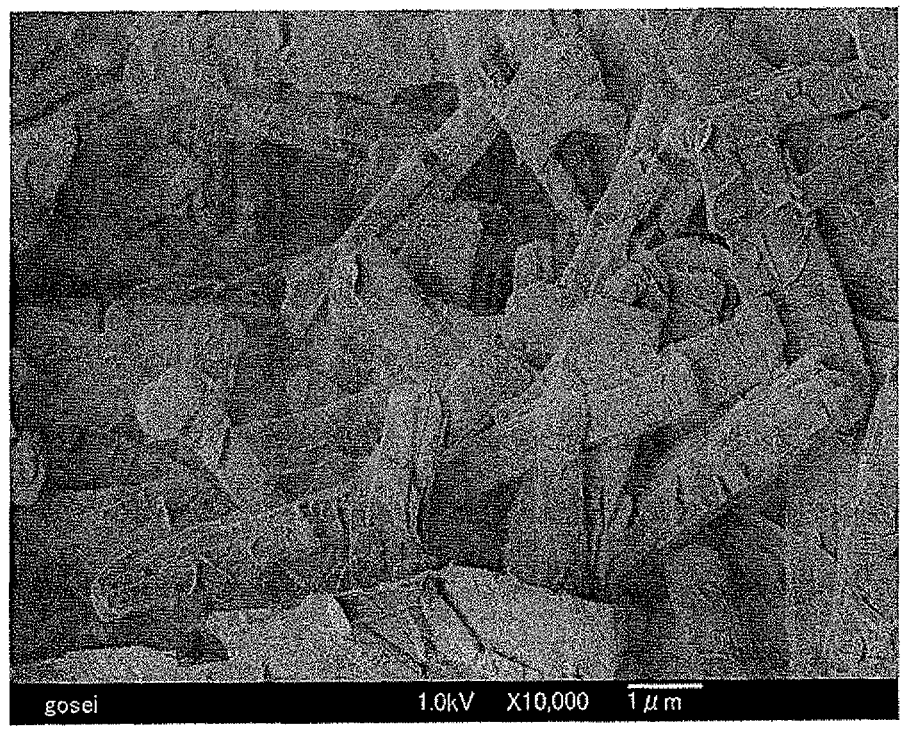
FIG. 14 is a scanning electron microscope (SEM) image of a phosphonic acid calcium salt produced in Comparative Example 5.

An SEM image of the obtained dry matter (powder) is shown in FIG. 14.

Comparative Example 6

To an 8% by mass aqueous calcium chloride solution (7.4 g of calcium chloride dihydrate and 66.2 g of water, pH 7.0), a 15% by mass aqueous phenylphosphonic acid solution (7.9 g of phenylphosphonic acid and 44.8 g of water, pH 0.5) was added dropwise with stirring to precipitate calcium phenylphosphonate. The suspension had a pH of 1.0. Subsequently, a 15% by mass aqueous sodium hydroxide solution (4.0 g of sodium hydroxide and 22.7 g of water) was added dropwise to the suspension with stirring to adjust the pH to be 12.0.

The obtained suspension was filtrated, and the obtained residue (wet matter) was then redispersed in 100 mL of water, followed by refiltration. These were repeated twice. The residue (wet matter) was then redispersed in 100 mL of acetone, followed by refiltration. These were repeated twice. Lastly the resultant was dried under reduced pressure at 20° C. to distill off acetone and was then dried at 200° C. for 12 hours.

Figure 15:
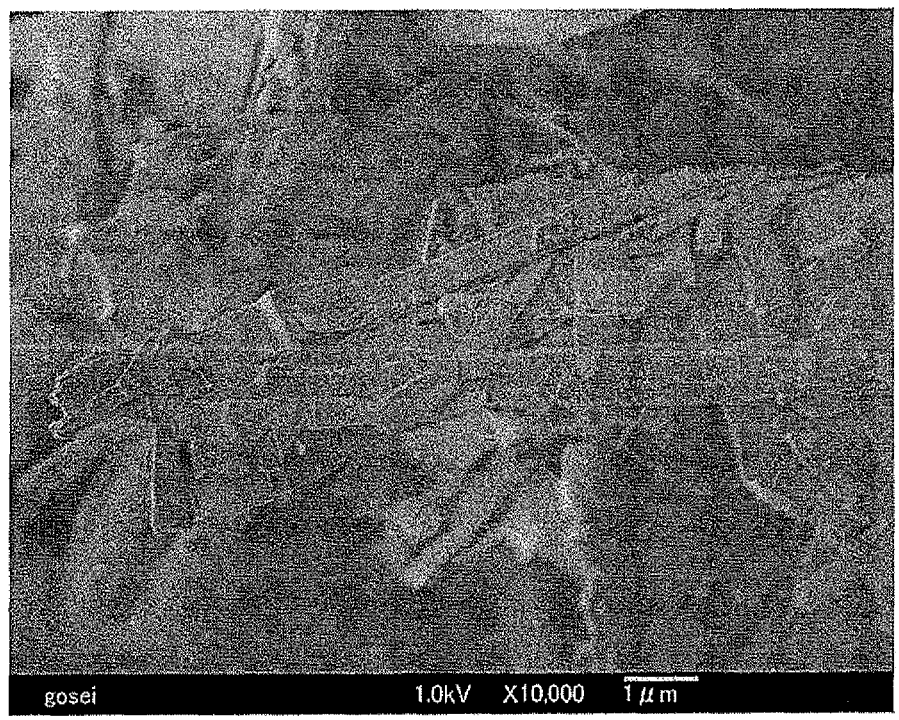
FIG. 15 is a scanning electron microscope (SEM) image of a phosphonic acid calcium salt produced in Comparative Example 6.

An SEM image of the obtained dry matter (powder) is shown in FIG. 15.

Comparative Example 7

To a 9% by mass aqueous calcium acetate solution (8.8 g of calcium acetate monohydrate and 79.3 g of water, pH 7.9), a 15% by mass aqueous phenylphosphonic acid solution (7.9 g of phenylphosphonic acid and 44.9 g of water, pH 0.5) was added dropwise with stirring to precipitate calcium phenylphosphonate. The suspension had a pH of 4.4.

Figure 16:
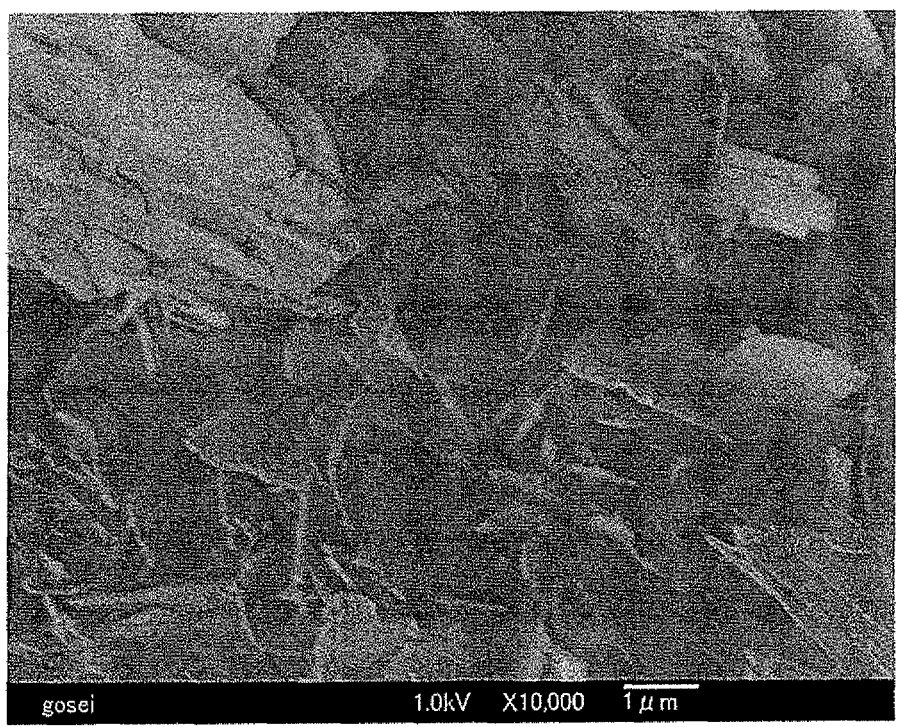
FIG. 16 is a scanning electron microscope (SEM) image of a phosphonic acid calcium salt produced in Comparative Example 7.

The obtained suspension was filtrated, and the obtained residue (wet matter) was then redispersed in 100 mL of water, followed by refiltration. These were repeated twice. The residue (wet matter) was then redispersed in 100 mL of acetone, followed by refiltration. These were repeated twice. Lastly the resultant was dried under reduced pressure at 20° C. to distill off acetone and was then dried at 200° C. for 12 hours. An SEM image of the obtained dry matter (powder) is shown in FIG. 16.

Comparative Example 8

To an 8% by mass aqueous calcium chloride solution (7.4 g of calcium chloride dihydrate and 66.2 g of water, pH 7.0), a 15% by mass aqueous phenylphosphonic acid solution (7.9 g of phenylphosphonic acid and 44.9 g of water, pH 0.5) was added dropwise with stirring to precipitate calcium phenylphosphonate. The suspension had a pH of 0.7.

The obtained suspension was filtrated, and the obtained residue (wet matter) was then redispersed in 100 mL of water, followed by refiltration. These were repeated twice. The residue (wet matter) was then redispersed in 100 mL of acetone, followed by refiltration. These were repeated twice. Lastly the resultant was dried under reduced pressure at 20° C. to distill off acetone and was then dried at 200° C. for 12 hours.

Figure 17:
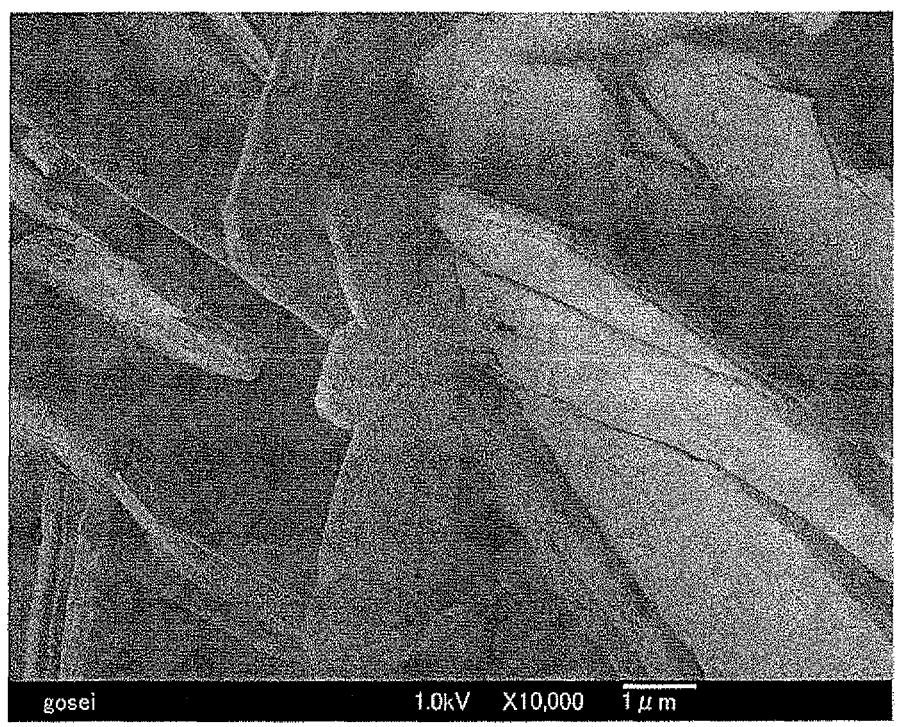
FIG. 17 is a scanning electron microscope (SEM) image of a phosphonic acid calcium salt produced in Comparative Example 8.

An SEM image of the obtained dry matter (powder) is shown in FIG. 17.

In each of Example 9 to Example 11 and Comparative Example 5 to Comparative Example 8, the average particle diameter of the calcium phenylphosphonate (dry matter) powder particle obtained was measured. The average particle diameter herein refers to the average length in the minor axis direction of the particles. The average particle diameter was obtained by randomly sampling 50 particles in an SEM image of dry matter to determine the average of approximately longest lengths in the minor axis direction of the particles. The results obtained are shown in Table 3.

TABLE 3

| | Metal source | Timing of base addition* | Washing solvent | Average particle diameter (μm) |
|---|---|---|---|---|
| Ex. 9 | Calcium chloride | PPA was initially neutralized | Water → acetone | 0.28 |
| Ex. 10 | Calcium acetate | PPA was initially neutralized | Water → acetone | 0.32 |
| Ex. 11 | Calcium chloride | PPA was initially neutralized | Water (→ dried under reduced pressure at 40° C.) | 0.28 |
| Comp. Ex. 5 | Calcium acetate | PPA was initially neutralized | Water alone | 0.59 |
| Comp. Ex. 6 | Calcium chloride | Added after salt precipitation | Water → acetone | 0.59 |
| Comp. Ex. 7 | Calcium acetate | No base used | Water → acetone | 0.70 |
| Comp. Ex. 8 | Calcium chloride | No base used | Water → acetone | 1.30 |

*PPA: phenylphosphonic acid

As shown in Table 3, the procedures of Example 9 to Example 11 each achieved an average particle diameter of 0.28 to 0.32 μM of calcium phenylphosphonate.

On the other hand, in Comparative Example 5 where calcium phenylphosphonate was precipitated under the same reaction condition as in Example 10, water alone was used as a washing solvent, and no organic solvent substitution was performed, the average particle diameter was 0.59 μm, which increased during drying.

In each of Comparative Example 6 where a base was used after salt precipitation and Comparative Example 7 and Comparative Example 8 where no base was used, the particle diameter exceeded 0.5 μm despite the fact that water as a washing solvent was substituted with an organic solvent.

The invention claimed is:

1. A method for producing phosphonic acid metal salt fine particles, comprising:
    a) causing a reaction of a phosphonic acid compound of Formula (I):

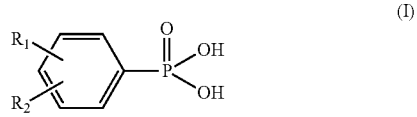

(where $R_1$ and $R_2$ are each independently a hydrogen atom, an alkyl group having 1 to 10 carbon atoms, or an alkoxycarbonyl group having 1 to 10 carbon atoms) with a base in an aqueous medium to adjust a pH range of the reaction system to be neutral to basic;
    b) causing a reaction of the product obtained in a) with a metal salt to precipitate a phosphonic acid metal salt from the aqueous medium;
    c) removing water from the phosphonic acid metal salt precipitated in b); and
    d) heating and drying the phosphonic acid metal salt from which water is removed in c),
    wherein the phosphonic acid metal salt is at least one metal selected from the group consisting of calcium salts and zinc salts.

2. The method for producing phosphonic acid metal salt fine particles according to claim 1, wherein
    in a) of adjusting the pH range of the reaction system to be neutral to basic, the reaction system is adjusted to be pH 7 to 14.

3. The method for producing phosphonic acid metal salt fine particles according to claim 1, wherein
    b) of precipitating a phosphonic acid metal salt from the aqueous medium is performed by adding the product obtained in a) dropwise to an aqueous solution of the metal salt.

4. The method for producing phosphonic acid metal salt fine particles according to claim 1, wherein
    c) of removing water from the precipitated phosphonic acid metal salt is performed by substituting water that is a reaction medium with an organic solvent.

5. The method for producing phosphonic acid metal salt fine particles according to claim 4, wherein
    the organic solvent is a water soluble organic solvent with a boiling point of 120° C. or less.

6. The method for producing phosphonic acid metal salt fine particles according to claim 5, wherein
    the organic solvent is methanol, ethanol, or acetone.

7. The method for producing phosphonic acid metal salt fine particles according to claim 1, wherein
    c) of removing water from the precipitated phosphonic acid metal salt is performed by drying under reduced pressure at 5 to 70° C.

* * * * *